(12) United States Patent
Champagne et al.

(10) Patent No.: US 9,539,084 B2
(45) Date of Patent: *Jan. 10, 2017

(54) DEVICES AND METHODS FOR TENDON REPAIR

(71) Applicant: Exsomed International IP, LLC, Avarua, Rarotonga (CK)

(72) Inventors: Lloyd P. Champagne, Phoenix, AZ (US); Jozef Zoldos, Phoenix, AZ (US)

(73) Assignee: Exsomed International IP. LLC, Avarua, Rarotonga (CK)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,657

(22) Filed: Mar. 6, 2015

(65) Prior Publication Data
US 2015/0182325 A1 Jul. 2, 2015

Related U.S. Application Data

(63) Continuation of application No. 13/648,019, filed on Oct. 9, 2012, now Pat. No. 9,017,404.
(Continued)

(51) Int. Cl.
*A61F 2/08* (2006.01)
*A61B 17/06* (2006.01)
(Continued)

(52) U.S. Cl.
CPC ............... *A61F 2/08* (2013.01); *A61B 17/04* (2013.01); *A61B 17/06* (2013.01); *A61B 17/0643* (2013.01); *A61B 17/06066* (2013.01); *A61B 17/06166* (2013.01); *A61B 17/1146* (2013.01); *A61B 17/122* (2013.01); *A61B 17/128* (2013.01); *A61F 2/0811* (2013.01);
(Continued)

(58) Field of Classification Search
CPC .......... A61F 2/08; A61F 2/0811; A61F 2/087
USPC .............................................. 623/13.11–13.2
See application file for complete search history.

(56) References Cited

U.S. PATENT DOCUMENTS

| 3,717,146 A | 2/1973 | Halloran |
| 4,471,777 A | 9/1984 | McCorkle |

(Continued)

FOREIGN PATENT DOCUMENTS

| CH | 643131 | 5/1984 |
| CH | 646858 | 12/1984 |

(Continued)

OTHER PUBLICATIONS

PCT; International Search Report and Written Opinion dated Sep. 17, 2010 in Application No. PCT/US2009/046662.
(Continued)

*Primary Examiner* — Suzette J Gherbi
(74) *Attorney, Agent, or Firm* — Snell & Wilmer LLP

(57) ABSTRACT

Disclosed is a device and method for repairing a partially or totally ruptured tendon. The device comprises an implant placed inside or outside of the tendon on either side of the rupture in order to strengthen the ruptured area during repair. Once positioned inside the tendon, the tendon is held in place so it can heal either by sewing or stapling through the tendon and implant, or by any other suitable method that utilizes the implant to provide strength to the ruptured area. In this manner the tendon can heal with less chance of rupturing again prior to healing.

46 Claims, 15 Drawing Sheets

Related U.S. Application Data

(60) Provisional application No. 61/589,526, filed on Jan. 23, 2012.

(51) Int. Cl.
| | |
|---|---|
| *A61B 17/064* | (2006.01) |
| *A61B 17/11* | (2006.01) |
| *A61B 17/122* | (2006.01) |
| *A61B 17/128* | (2006.01) |
| *A61B 17/04* | (2006.01) |

(52) U.S. Cl.
CPC .......... *A61B 2017/0641* (2013.01); *A61B 2017/0648* (2013.01); *A61B 2017/06057* (2013.01); *A61B 2017/06176* (2013.01); *A61F 2002/087* (2013.01); *A61F 2002/0858* (2013.01); *A61F 2250/0067* (2013.01)

(56) References Cited

U.S. PATENT DOCUMENTS

| | | | |
|---|---|---|---|
| 4,584,722 A | 4/1986 | Levy et al. | |
| 4,781,191 A | 11/1988 | Thompson | |
| 4,901,717 A | 2/1990 | Moore et al. | |
| 4,909,789 A | 3/1990 | Taguchi et al. | |
| 5,312,255 A | 5/1994 | Bauer | |
| 5,667,510 A | 9/1997 | Combs | |
| 5,690,633 A | 11/1997 | Taylor et al. | |
| 5,853,413 A | 12/1998 | Carter et al. | |
| 6,187,007 B1 | 2/2001 | Frigg | |
| 6,221,006 B1 | 4/2001 | Dubrul et al. | |
| 6,231,319 B1* | 5/2001 | Iida | F04C 18/10 417/437 |
| 6,231,413 B1* | 5/2001 | Tsukamoto | H01J 1/316 445/24 |
| 6,306,140 B1 | 10/2001 | Siddiqui | |
| 6,475,242 B1 | 11/2002 | Bramlet | |
| 6,592,623 B1* | 7/2003 | Bowlin | A61F 2/08 623/13.17 |
| 6,607,530 B1 | 8/2003 | Carl et al. | |
| 6,808,526 B1 | 10/2004 | Magerl et al. | |
| 7,041,106 B1 | 5/2006 | Carver et al. | |
| 7,988,724 B2 | 8/2011 | Salahieh et al. | |
| 8,597,337 B2 | 12/2013 | Champagne | |
| 8,864,804 B2 | 10/2014 | Champagne et al. | |
| 9,017,404 B2* | 4/2015 | Champagne | A61F 2/0811 623/13.11 |
| 2001/0049529 A1 | 12/2001 | Cachia et al. | |
| 2002/0045897 A1 | 4/2002 | Dixon et al. | |
| 2002/0055747 A1 | 5/2002 | Cano et al. | |
| 2002/0055749 A1* | 5/2002 | Esnouf | A61F 2/08 606/148 |
| 2002/0143337 A1 | 10/2002 | Orbay et al. | |
| 2002/0198527 A1 | 12/2002 | Muckter | |
| 2003/0083661 A1 | 5/2003 | Orbay et al. | |
| 2004/0260288 A1 | 12/2004 | Means | |
| 2005/0075642 A1 | 4/2005 | Felt et al. | |
| 2005/0107791 A1 | 5/2005 | Manderson | |
| 2006/0129153 A1 | 6/2006 | Klaue et al. | |
| 2006/0195099 A1 | 8/2006 | Bottlang | |
| 2007/0027547 A1 | 2/2007 | Rydell et al. | |
| 2007/0135816 A1 | 6/2007 | Kropf et al. | |
| 2007/0282342 A1 | 12/2007 | Niederberger et al. | |
| 2008/0249547 A1 | 10/2008 | Dunn | |
| 2008/0249574 A1 | 10/2008 | McCombs et al. | |
| 2009/0062868 A1 | 3/2009 | Casutt | |
| 2010/0106254 A1 | 4/2010 | Delsignore | |
| 2010/0121136 A1 | 5/2010 | Champagne | |
| 2010/0130978 A1 | 5/2010 | Orbay et al. | |
| 2010/0312286 A1 | 12/2010 | Dell'Oca | |
| 2010/0324556 A1 | 12/2010 | Tyber et al. | |
| 2011/0130794 A1 | 6/2011 | Vaidya | |
| 2012/0083847 A1 | 4/2012 | Heubner et al. | |
| 2012/0221104 A1* | 8/2012 | Altman | A61F 2/08 623/8 |
| 2012/0253464 A1* | 10/2012 | Hwang | A61F 2/08 623/13.18 |
| 2012/0253465 A1* | 10/2012 | Missos | A61F 2/08 623/13.19 |
| 2013/0053961 A1* | 2/2013 | Derwin | A61F 2/08 623/13.17 |
| 2013/0060333 A1* | 3/2013 | Gonzalez-Hernandez | A61F 2/0811 623/13.15 |
| 2013/0165979 A1 | 6/2013 | Greenberg et al. | |
| 2013/0261662 A1* | 10/2013 | Mayer | A61L 17/00 606/228 |
| 2013/0274879 A1 | 10/2013 | Champagne et al. | |
| 2014/0067063 A1 | 3/2014 | Bonutti | |
| 2015/0094722 A1 | 4/2015 | Champagne et al. | |
| 2015/0094724 A1 | 4/2015 | Champagne et al. | |
| 2015/0094777 A1 | 4/2015 | Champagne et al. | |
| 2015/0173737 A1* | 6/2015 | Champagne | A61F 2/0811 606/228 |

FOREIGN PATENT DOCUMENTS

| | | |
|---|---|---|
| DE | 102007003645 | 7/2008 |
| EP | 2713386 | 11/1978 |
| EP | 0597223 | 5/1994 |
| EP | 1378205 | 1/2004 |
| EP | 2606843 | 6/2013 |
| GB | 2007099 | 5/1979 |
| GB | 2181356 | 4/1987 |
| WO | WO9733537 | 9/1997 |
| WO | WO2004093700 | 4/2004 |
| WO | WO2005092226 | 10/2005 |
| WO | WO2006105935 | 12/2006 |
| WO | WO2007081601 | 7/2007 |
| WO | WO2007109140 | 9/2007 |
| WO | WO2008063156 | 5/2008 |
| WO | WO2010151589 | 12/2010 |
| WO | WO2014011933 | 1/2014 |
| WO | WO2015050895 | 9/2015 |
| WO | WO2015050896 | 9/2015 |
| WO | WO2015050898 | 9/2015 |
| WO | WO2015050902 | 9/2015 |

OTHER PUBLICATIONS

EP; Examination Report dated May 30, 2011 in Application No. EP 09774002.1.
USPTO; Office Action dated Oct. 4, 2011 in U.S. Appl. No. 12/372,712.
USPTO; Office Action dated Mar. 21, 2012 in U.S. Appl. No. 12/480,676.
EP; Examination Report dated May 25, 2012 in Application No. EP 09774002.1.
USPTO; Office Action dated May 29, 2012 in U.S. Appl. No. 12/372,712.
USPTO; Office Action dated Sep. 18, 2012 in U.S. Appl. No. 12/480,676.
USPTO; Office Action dated Mar. 22, 2013 in U.S. Appl. No. 12/372,712.
USPTO; Notice of Allowance dated Jul. 30, 2013 in U.S. Appl. No. 12/372,712.
PCT; International Search Report and Written Opinion dated Sep. 9, 2013 in Application No. PCT/US2013/050155.
USPTO; Office Action dated Sep. 24, 2013 in U.S. Appl. No. 12/480,676.
USPTO; Office Action dated Feb. 18, 2014 in U.S. Appl. No. 13/555,933.
USPTO; Notice of Allowance dated Jun. 25, 2014 in U.S. Appl. No. 13/555,933.
USPTO; Office Action dated Aug. 29, 2014 in U.S. Appl. No. 13/648,019.
PCT; International Search Report and Written Opinion dated Dec. 10, 2014 in Application No. PCT/US2014/058463.
PCT; International Search Report and Written Opinion dated Dec. 12, 2014 in Application No. PCT/US2014/058474.

(56) References Cited

OTHER PUBLICATIONS

USPTO; Notice of Allowance dated Dec. 31, 2014 in U.S. Appl. No. 13/648,019.
PCT; International Search Report and Written Opinion dated Jan. 20, 2015 in Application No. PCT/US2014/058448.
PCT; International Search Report and Written Opinion dated Feb. 9, 2015 in Application No. PCT/US2014/058441.
USPTO; Office Action dated Sep. 22, 2015 in U.S. Appl. No. 14/503,228.
USPTO; Office Action dated Oct. 5, 2015 in U.S. Appl. No. 13/940,173.
USPTO; Final Office Action dated May 2, 2016 in U.S. Appl. No. 14/503,228.
USPTO; Final Office Action dated May 23, 2016 in U.S. Appl. No. 14/640,657.

\* cited by examiner

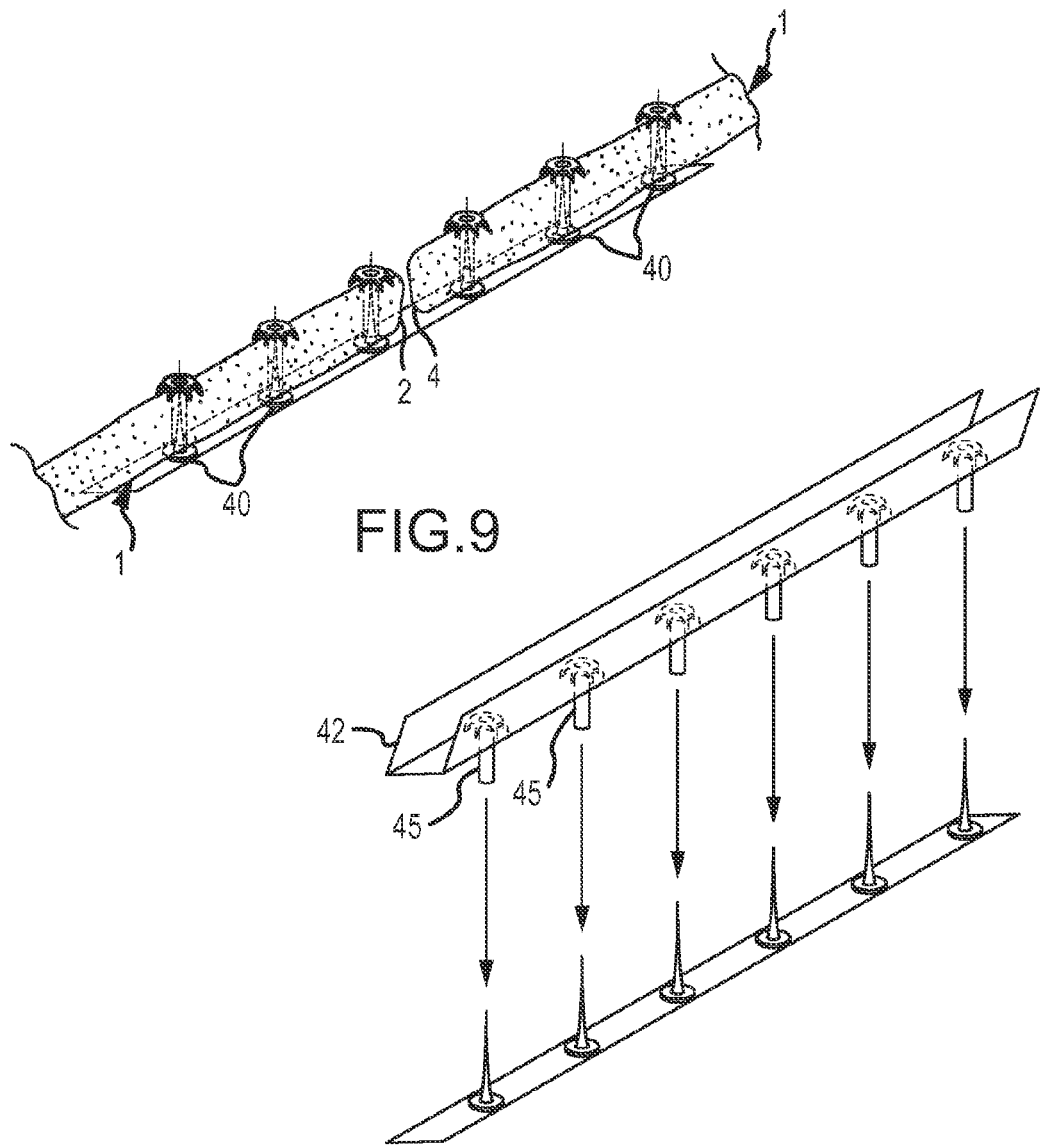

DEVICES AND METHODS FOR TENDON REPAIR

CROSS-REFERENCE TO RELATED APPLICATIONS

This application in a continuation of U.S. patent application Ser. No. 13/648,019 entitled "DEVICES AND METHODS FOR TENDON REPAIR," filed on Oct. 9, 2012, which claims priority to U.S. Provisional Patent Application Ser. No. 61/589,526 entitled "TENDON REPAIR DEVICE AND METHOD," filed on Jan. 23, 2012, the disclosures of which are incorporated herein by reference.

FIELD OF THE INVENTION

The present invention relates to a device and method for repairing a ruptured tendon that reduces the likelihood of the tendon being partially or completely ruptured again while healing.

BACKGROUND OF THE INVENTION

When a tendon is partially or totally ruptured or severed (collectively, "a rupture"), the two ends of the tendon where the rupture occurred are reattached surgically. In practice, this is accomplished by a surgeon stitching (i.e., suturing) the two ends together. The suturing can be done in any suitable manner, as there have been many demonstrated techniques of suture repair. A problem with these standard suture techniques is that the sutured tendon is relatively weak until the tendon is fully healed and the tendon can rupture if the force applied to the repaired tendon exceeds the strength of the repair.

SUMMARY OF THE INVENTION

The invention comprises an implant placed inside or outside a ruptured tendon on both sides of the rupture in order to strengthen the tendon repair of the ruptured area during healing. Once positioned inside or outside the tendon the implant and tendon are secured together by sewing or stapling through the tendon and implant, or by any other suitable method (including staples, tacks or rivets) that utilizes the implant to provide strength to the ruptured area. In this manner the tendon can heal with less chance of rupturing again prior to healing.

Instead of an internal implant, each end of the ruptured tendon may be positioned inside a tube (or other type of external implant) and retained there in order for the tendon to heal. Again, the material forming the external implant adds strength to the ruptured area to help prevent the tendon from rupturing again prior to healing. The tendon and external implant can be secured together by any physical means, such as those as noted above.

Methods of using tendon repair devices according to the invention are also disclosed herein.

BRIEF DESCRIPTION OF THE DRAWINGS

FIG. 9 shows an embodiment wherein needles or spikes are used to temporarily or permanently secure the ruptured area of a tendon in place.

FIG. 10 shows rivets that could be used to secure an insert in place in a tendon for repair.

DETAILED DESCRIPTION OF PREFERRED EMBODIMENTS

Figure 1:
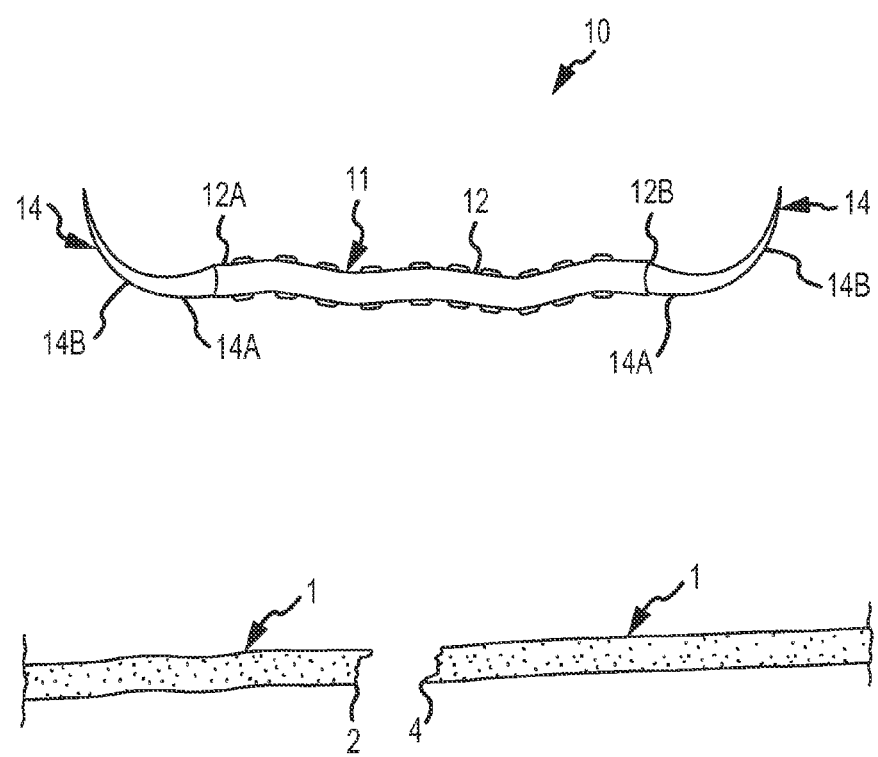
FIG. 1 shows an embodiment of a device according to the invention.
Figure 2A:
FIGS. 2A-2C show an embodiment of a needle according to the invention.
Figure 2B:
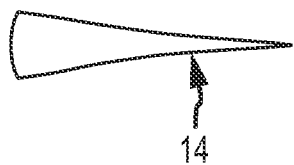
Figure 2C:

Turning now to the Figures, where the purpose is to describe a preferred embodiment of the invention and not to limit same, FIG. 1 shows a tendon repair device 10 according to an aspect of the invention. Device 10 has a support implant 11 having a body portion 12, with a first end 12A and second end 12B. The function of support implant 11 is to be inserted into each end of a ruptured tendon 1 so as strengthen the repair to the rupture in order to help prevent the tendon from rupturing again prior to healing. Once ruptured, the tendon has a first end 2 and another, second end 4. The two ends must be connected to repair the rupture.

Implant 11 can be formed of any suitable bio-absorbable or non-bio-absorbable material, and Implant may be a mesh like or cloth like, flexible material. Textured edges, scalloping or other physical characteristics may be present on implant 11 to increase its friction with the tendon to help prevent slippage. For example, implant 11 may have an outer surface having one of a: spiraled configuration, a cruciate cross section, and a plurality of outwardly-extending ribs.

In one preferred embodiment, implant 11 comprises standard suture material, which is either absorbable or nonabsorbable. Such material includes threads that may be monofilament or polyfilament braid or weave formed in approximately a 6 cm×3 mm mesh. The insert may be tubular, or generally flat, or of any suitable configuration.

Exemplary embodiments of implants according to various aspects of the invention may include a fabric material. Such fabric material may be woven, knitted, braided, and/or twisted. The fabric may comprise any desired combination of absorbable and non-absorbable materials, including silk, cotton, metal, and/or synthetic fibers. The fabric may be of any suitable size, shape, thickness, and density.

Examples of absorbable materials that may be used in conjunction with embodiments of the invention include polyglactin, polycaprolate, poliglecaprone, polysorb, polyglygolic acid, polylactic acid, polydioxanone, caprolactone, collagen, surgical gut, and combinations thereof. Examples of non-absorbable materials that may be used in conjunction with embodiments of the invention include polypropylene, polyester, nylon, silk, cotton, metal, and combinations thereof.

The implant 11 could also be pretreated with an antibiotic or growth enhancing substance. There are many commercially-available pharmacological agents such as antibiotics and therapeutic agents such as growth hormones and/or bioactive molecules that may accelerate tendon healing. Additionally, non-bioactive products may be incorporated into the implant to physically strengthen the repair.

Figure 8:
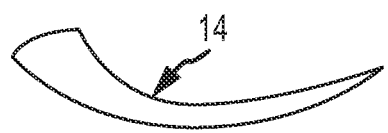
FIG. 8 depicts a needle according to the invention.

In the preferred embodiment, end 12A and 12B are each attached to a separate needle 14. Each needle 14 is for being inserted into one of the ends of the ruptured tendon 1 and to pull body portion 12 of implant 11 into the first end 2 of the tendon and the second end 4 of the tendon, respectively. Any suitable needle or other device may be used for this purpose. It is preferred, however, that the needle have a shape that predetermines how far it penetrates along the length of each end of the tendon 1. In the embodiment shown, each needle 14 has a relatively straight portion 14A and a curved portion 14B, as best seen in FIGS. 1 and 8. Other devices for insertion of an insert 11 could be used, such as reamers designed to open a path in the tendon for insert placement.

The size and shape of needle 14 is determined by the size and shape of the particular implant. In this current depiction, the dimensions of needle 14 are 2 cm in length and 3 mm wide at the portion to which the implant 11 is attached. The size and shape of needle 14 depends on the size of the tendon to be repaired and the type of implant used to support the ruptured area of the tendon. Different needle lengths and sizes may be required for different size tendons and different space requirements within the body.

Implant 11 has an outer surface 16. Outer surface 16 preferably has a surface that creates friction with the inner part of the tendon 1, which outer surface 16 will contact when inserted into tendon 1. The purpose of the friction is to bind implant 11 with the tendon to help insure the two do not separate and thus to help strengthen the support provided by implant 11 at the rupture site.

Figure 3A:
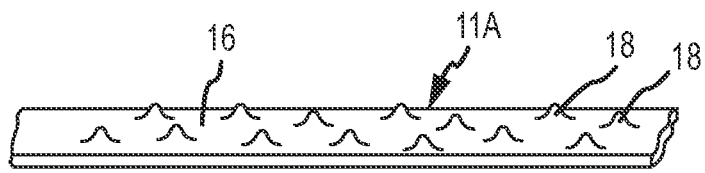
FIG. 3A-3D show various implants having surface textures and material configurations according to aspects of the invention.

The outer surface 16 of implant 11 may have any one of or combination of configurations to create friction. In the embodiment shown in FIG. 3A the outer surface includes stiplets 18. In a preferred embodiment, the stiplets 18 are between 1 mm and 2 mm in height (as measured according to the distance from the main portion 16A of the outer surface), and most preferably about 0.5-2 mm in height. The size of the stiplets may vary, however, according to the size of the tendon and type of rupture being repaired. For example, the stiplets may be between 0.5 mm and 4 mm in height and between 0.5 mm and 4 mm in diameter at the base.

Figure 3B:
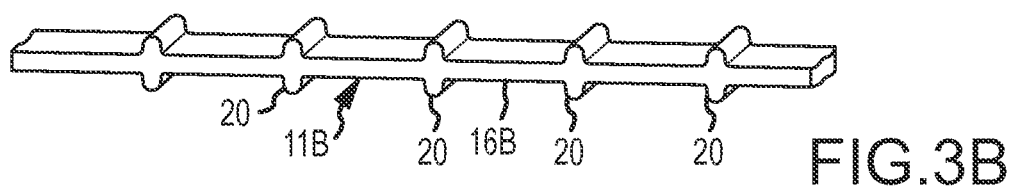
Figure 15:
FIG. 15 shows an alternative shaped insert that may be used inside of a tendon.

It is preferred that each stiplet 18 is between 0.5-5 mm in distance from the next closest stiplet 18, although any suitable distance may be selected. The implant could resemble a string of pearls (as shown in FIGS. 3B and 15) which would have relatively large variations between the larger stiplets and the smaller size of the implant between the stiplets. It is also possible that implant 11 could have a co-figuration such as a stiplets on a tape strip or cord that might be, for example, 3 mm wide by 1 mm thick and have with stiplets on either or both sides, or have a top and/or bottom surface that is microtextured in any manner, and may simply be the surface of a coarse, braided cloth material.

Figure 3C:
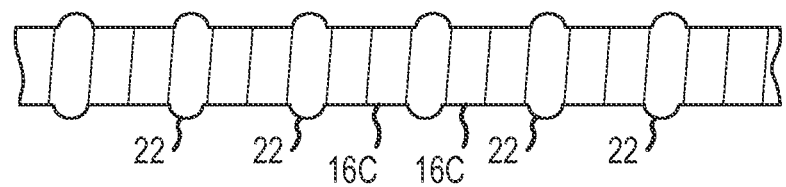

FIGS. 3B and 3C show implants that have ribbed outer surfaces. In FIG. 3B the diameter of the main portion 16B of the outer surface is relatively narrow, and each rib 20 has a height of approximately 0.5 mm as measured from the main portion 16B, although any suitable height may be utilized, such as between 1 mm-8 mm.

In FIG. 3C the diameter of the main portion 16C is larger than the diameter of main portion 16B, and each rib 22 has a height of approximately 0.5 mm as measured from the main portion 16C, although any suitable height may be utilized, such as between 1 mm-8 mm.

Figure 3D:
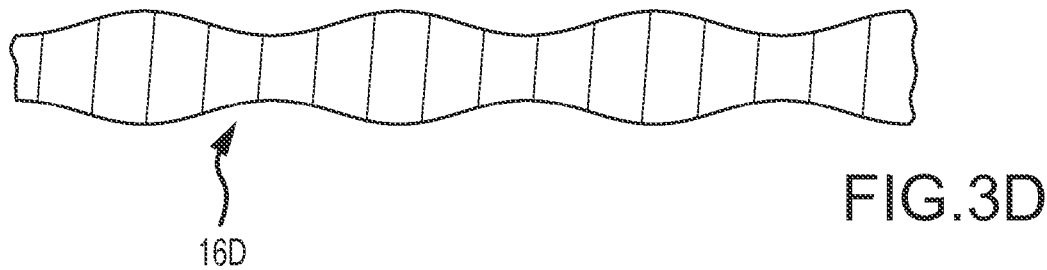

FIG. 3D shows an implant with a serpentine outer wall 16D. In this embodiment, the variation between the smallest diameter of the implant and the lowest is about 0.5 mm to about 4 mm, although any suitable dimensions, for example between 1 mm and 2 mm to 5 mm, or 2 mm and 3 mm to 5 mm, may be used.

Figure 14:
FIG. 14 shows an insert according to an aspect of the invention that includes directional barbs that help prevent the insert from being dislodged from the tendon.

It is also possible to combine any of the concepts shown in FIGS. 3A-3D, 14 and 15. For example, the implant 11 could have a serpentine outer wall and also include stiplets and/or ribs. Further, the implant may include backward angled barbs that allow the implant to be pulled through the tendon, but that resist removal when pulled in a direction against the barbs, as shown in FIG. 14.

Once the implant 11 in positioned into each end 2 and 4 of the ruptured tendon 1, the two ends 2 and 4 of the tendon 1 and the implant 11 are mechanically attached in any suitable manner, such as by suturing, stapling, or using surgical rivets or pins.

Figure 4:
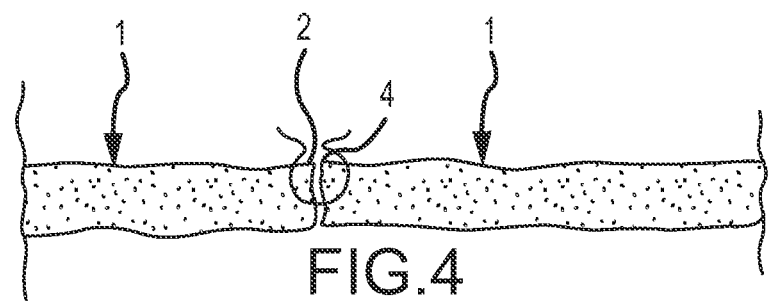
FIG. 4 depicts the first step in positioning a device according to the invention in a ruptured tendon.
Figure 5:
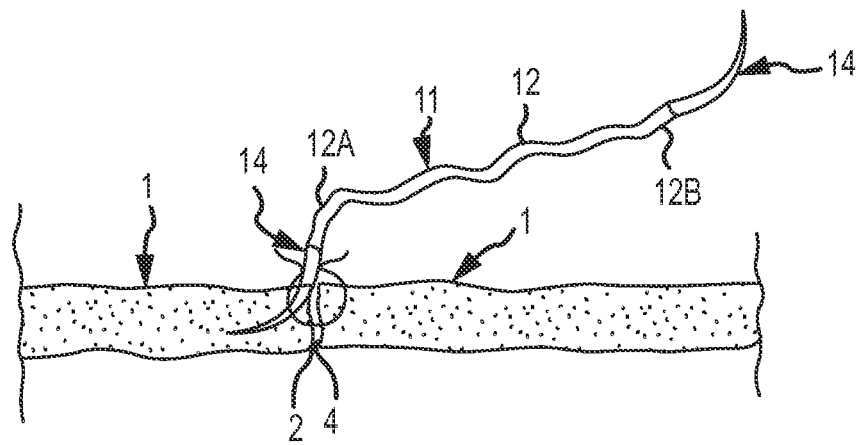
FIG. 5 depicts a second step in positioning a device according to the invention in a ruptured tendon.
Figure 6A:
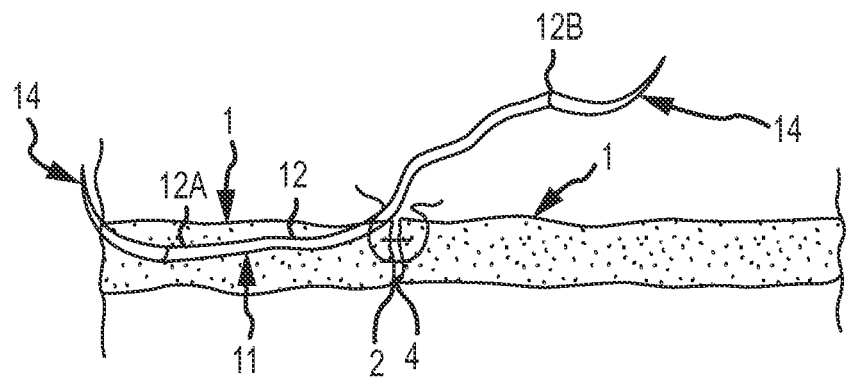
FIGS. 6A-6C depicts a third step in positioning a device according to the invention in a ruptured tendon.
Figure 6B:
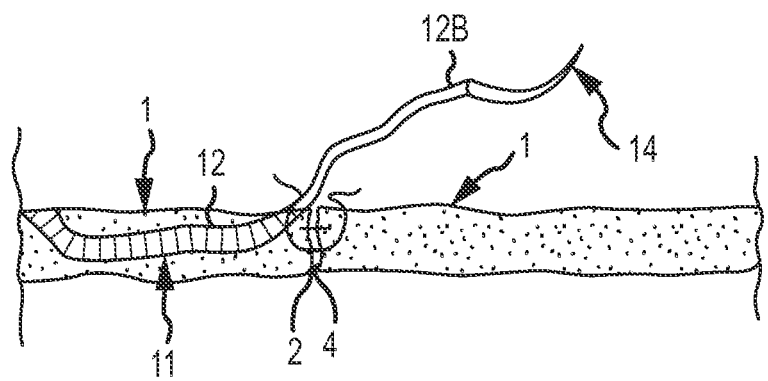
Figure 6C:
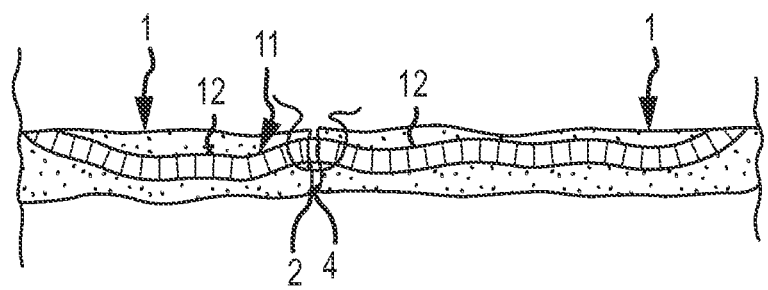

One method of effectuating a repair is shown in FIGS. 4-7. FIG. 4 shows ends 2 and 4 of ruptured tendon 1 being initially attached with a suture. FIG. 5 shows a needle 14 with end 12A of implant 11 attached thereto being pushed through first end 2 of tendon 1. This pulls part of the body portion 12 into the first end 2. When the needle 14 passes through the outer surface of tendon 1 it pulls the implant 11 with it. The implant material is cut away from the needle 14, and preferably close to the outer surface of the tendon 1.

This same procedure is repeated on end 4 of tendon 1.

Figure 7:
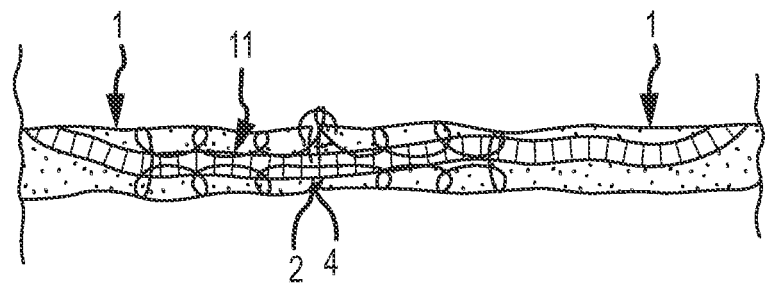
FIG. 7 depicts a fourth step in positioning a device according to the invention in a ruptured tendon.

Once the implant 11 is positioned in tendon 1, the ruptured ends on the tendon and the implant are mechanically attached. As shown in FIG. 7, this is done using any of the known tendon suturing techniques. Any suitable technique, however, such as a suturing technique, stapling, or other mechanical method of attachment could be utilized. Adhesive might be used to augment the repair. In this manner, the implant adds significant strength to the rupture area and helps to prevent it from rupturing or pulling apart partially to create a gap under a load prior to healing.

Figure 16:
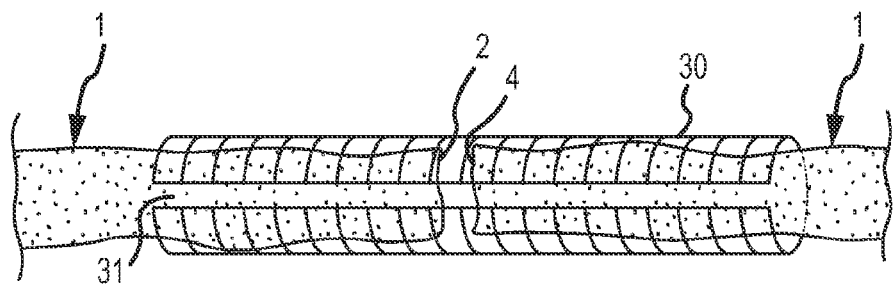
FIG. 16 shows an insert that is positioned outside of the tendon.
Figure 17:
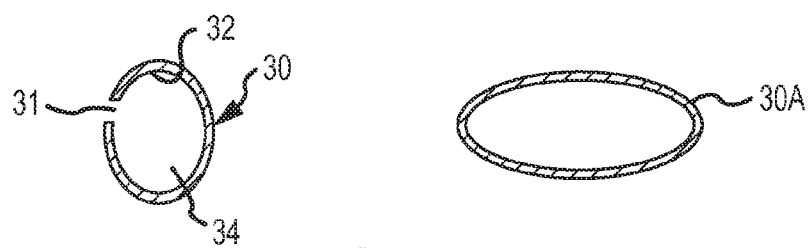
FIG. 17 shows two cross-sectional views of inserts that may be positioned outside of a tendon.

An alternate implant 30 is shown in FIGS. 16 and 17. Implant 30 is a hollow tube into which the first end 2 and second end 4 of the ruptured tendon 1 are placed so they touch, and are preferably pressed together. In this embodiment, there is an opening 31 along one side of insert 30 to make placement of insert 30 around tendon 1 simple. The implant 30 has an inner surface 32 defining a cavity 34 that is dimensioned to receive each end 2 and 4 of ruptured tendon 1. The tendon ends 2 and 4, and the implant 30 would then be mechanically attached with any of the prior mentioned suture techniques, staples, rivets, pins, clamps, or in any suitable manner. Additionally, inner surface 32 may include apparatus 36 that enables each end 2 and 4 of tendon 4 to be inserted into cavity 34, and that tend to hold the ends of the tendon in place and resist the ends 2 and 4 from being removed from cavity 34.

Figure 17A:
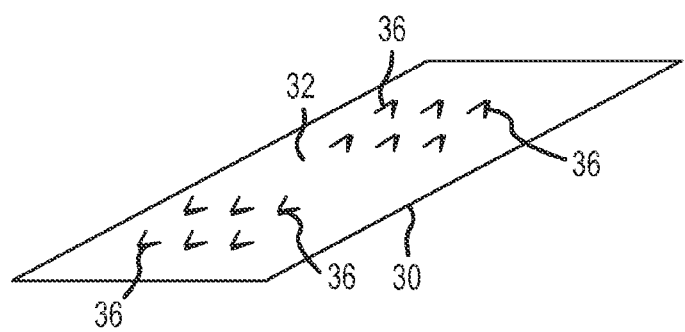
FIG. 17A is a view of an embodiment of the insert of FIG. 16 laid out flat to show its interior surface.

For example, inner surface 32 could have structures 36 that are backward-facing ribs or barbs as shown in FIG. 17A, which could extend any suitable distance outward from inner surface 32. Such structures could, for example, extend between 0.5 mm to 2 mm from inner surface 32.

Once the ends 2 and 4 of tendon 1 have been inserted into implant 30, the ends and implant 30 are mechanically attached in the manner previously described with respect to implant 11.

Alternatively, an implant placed on the outside of tendon 1 may not have any openings, such as opening 31, as shown in cross-sectional view 30A.

FIG. 9 shows needles 40 that can be used to secure a tendon in place with ends 2 and 4 juxtaposed prior to or after an insert 11 or insert 30 has been placed in or on the tendon 1 and secured thereto.

FIG. 10 depicts staples or rivets 45 that are placed by a stapler 42 to secure a tendon and insert inside of or outside the tendon according to methods and structures of the invention.

Figure 11:
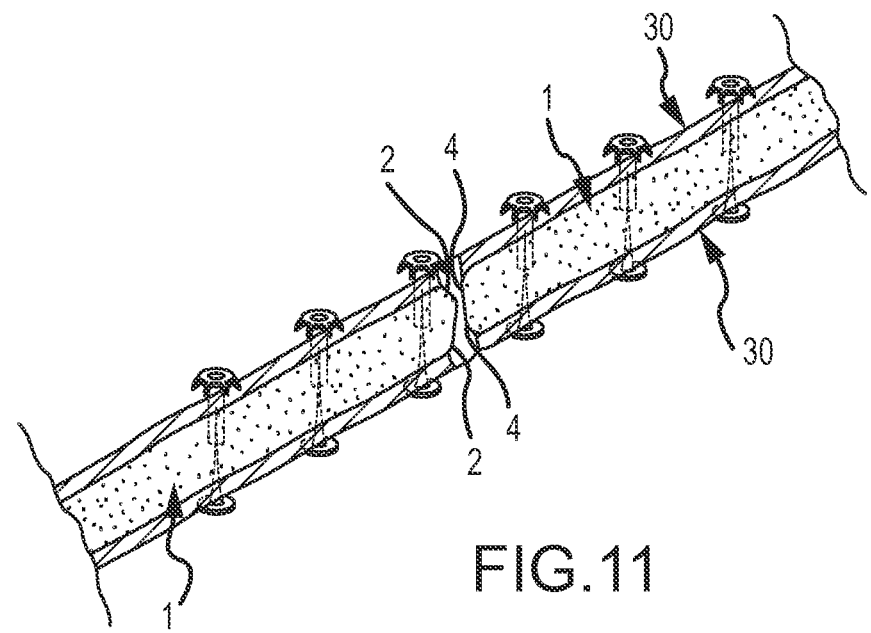
FIG. 11 shows rivets of the type shown in FIG. 10 that could be used to secure an insert inside of or outside of a tendon.

FIG. 11 shows rivets 45 positioned through an outer insert 30 and through a tendon 1 to hold insert 30 and ruptured ends 2 and 4 in place.

Figure 12:
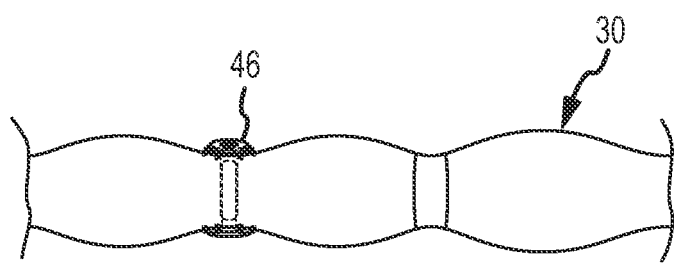
FIG. 12 shows another type of fastener that may be used to secure an insert inside of or outside of a tendon.

FIG. 12 shows another type of rivet 46 that can be used to secure a ruptured tendon and insert in position.

Figure 13:
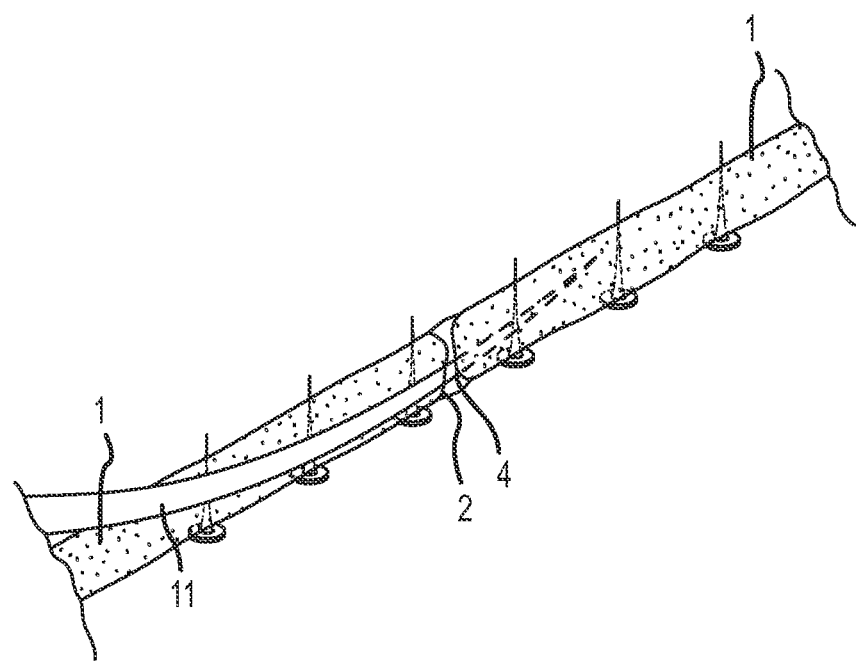
FIG. 13 shows a tendon that is first secured over spikes or needles and a knife that goes through the tendon to pull an insert through the tendon and the rupture.

FIG. 13 shows a method and structure by which a ruptured tendon 1 is secured on spikes 50 to hold it in place. As shown in this Figure, a knife or needle is pushed through tendon 1 to pull insert 11 therethrough to strengthen the rupture area at ends 2 and 4. The tendon 1 and insert 11 are then mechanically secured using any of the techniques described herein. However, pins or spikes may be used to secure a tendon in place prior to repair using several of the techniques described herein.

FIGS. 14 and 15, which have previously been described, show alternate embodiments of insert 11 that is positioned inside of tendon 1 to effectuate a rupture repair.

Figure 18:
FIGS. 18-20 show different embodiments of an insert that may be used inside of a tendon.
Figure 19:
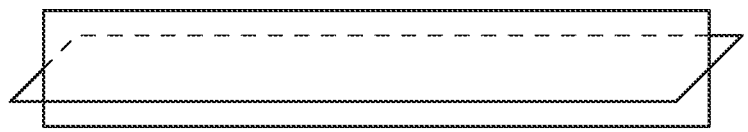
Figure 20:
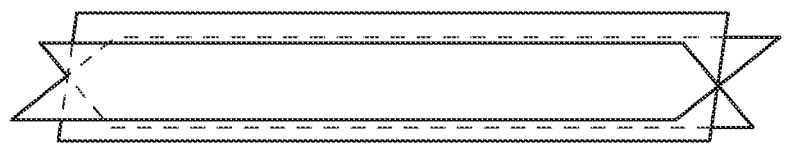

FIGS. 18-20 show alternate configurations of insert 11 that may be positioned inside of tendon 1 to effectuate a rupture repair. Any of these embodiments may include structures such as stiplets, ribs, barbs or textured surfaces to secure them inside of a tendon 1.

Figure 21:
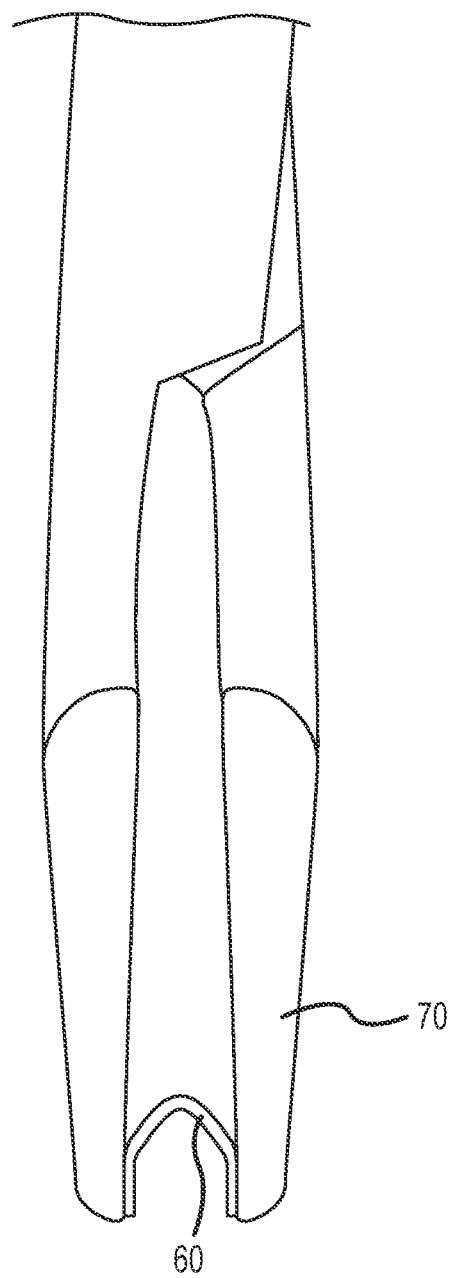
FIGS. 21 and 22 show a clamp and tool used to position and crimp the clamp that can be used to secure an insert according to the invention.
Figure 22:
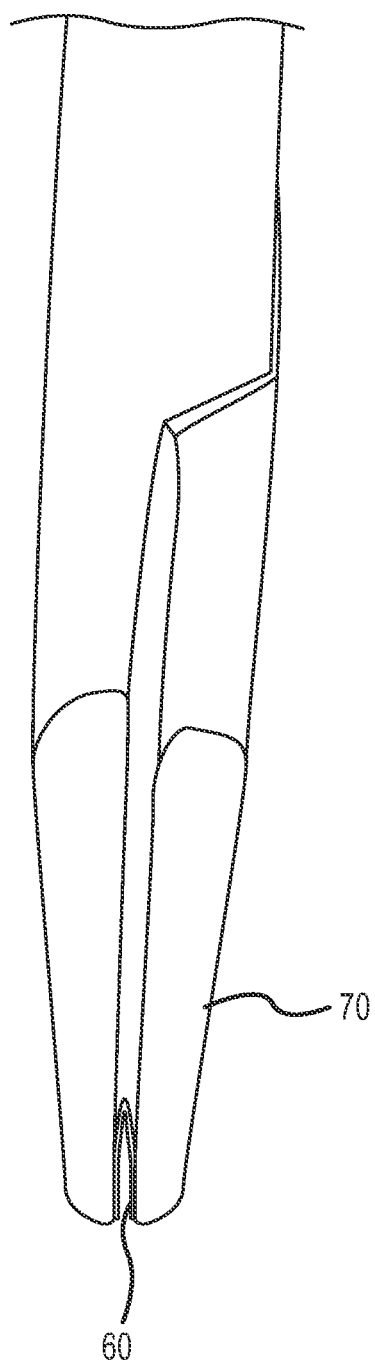

FIGS. 21-22 show a clamp 60 according to the invention and a tool 70 that may be used to position and compress clamp 60. Clamp 60 and tool 70 are known to those skilled in the art.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A tendon repair device for being positioned inside of a tendon that includes a partial or complete rupture, the rupture separating the tendon into a first section and a second section, the tendon repair device including:
   an implant having a body that is configured to be inserted into the first section of the tendon, and into the second end of the tendon;
   the implant having an outer surface that that grips the tendon into which the implant is inserted; and
   the outer surface having one of a the group consisting of: a spiraled configuration, a criss cross or cruciate pattern in cross section, and a plurality of ribs extending from the outer surface.

2. The tendon repair device of claim 1 wherein the implant is comprised of biodegradable or non-biodegradable material.

3. The tendon repair device of claim 1 wherein the implant is comprised of a mesh.

4. The tendon repair device of claim 3 wherein the implant is a mesh having mesh dimensions of approximately 6 cm×3 mm.

5. The tendon repair device of claim 1 wherein the implant further comprises a series of stiplets.

6. The tendon repair device of claim 1 that has a hollow interior.

7. The tendon repair device of claim 1 that includes an antibiotic to inhibit the growth of bacteria.

8. The tendon repair device of claim 7 that is made of a material and the antibiotic is included within the material.

9. The tendon repair device of claim 7 that is made of a material and wherein the antibiotic is coated on the material.

10. The tendon repair device of claim 1 that includes a growth enhancing agent.

11. The tendon repair device of claim 10 that is impregnated with a growth enhancing agent.

12. The tendon repair device of claim 1 that has a hollow interior and textured interior surface.

13. The tendon repair device of claim 1 wherein the outer surface has outwardly extending ribs that are spaced apart 0.5-3 mm or less.

14. The tendon repair device of claim 5 wherein each stiplet extends about 0.5-2 mm from the rest of the outer surface.

15. The tendon repair device of claim 5 wherein each stiplet is spaced about 0.5-2 mm from the next closest stiplet.

16. The tendon repair device of claim 1 wherein the outer surface further includes wide areas alternating with narrow areas.

17. The tendon repair device of claim 16 wherein there is a difference in diameter between each narrow area and each wide area, and the difference in diameter is between 0.5 mm and 4 mm.

18. The tendon repair device of claim 1 that includes openings for receiving a needle, a staple, a rivet or another solid structure.

19. The tendon repair device of claim 1 that has a body portion, a first end and a second end, and a needle attached to the first end.

20. The tendon repair device of claim 19 that has a needle attached to the second end.

21. The tendon repair device of claim 19 wherein the needle attached to the first end has a curved portion and a straight portion, and is designed to imbed the insert a predetermined distance into the tendon.

22. The tendon repair device of claim 20 wherein the needle attached to the second end has a curved portion and a straight portion, and is designed to imbed the insert a predetermined distance into the tendon.

23. The tendon repair device of claim 19 wherein the needle is configured to imbed the body of the implant 0.5 cm to 5 cm inside each end of the tendon.

24. The tendon repair device of claim 23 wherein the needle has a wide enough base to match the width of the implant to connect to the body portion.

25. A tendon repair device for repairing a tendon that has been ruptured into a first end and a second end, the device comprising a hollow tube having a first end and second end, wherein the first end of the tendon is received in the first end of the hollow tube and the second end of the tendon is received in the second end of the hollow tube.

26. The tendon repair device of claim 25 wherein the hollow tube has an inner surface that includes raised portions that retain the first end of the tendon and the second end of the tendon.

27. The tendon repair device of claim 26 wherein the raised portions comprise one or more of: ribs, backward angled ribs, barbs, and backward angled barbs, and stiplets.

28. The tendon repair device of claim 26 that has an interior diameter of between 2 mm and 20 mm.

29. The tendon repair device of claim 26 wherein the raised portions extend .5 mm-5 mm from the inner surface.

30. The tendon repair device of claim 26 that is physically connected to the tendon by one or more of sutures, staples, rivets, or clamps to help retain the ends of the tendon within the implant.

31. The tendon repair device of claim 26 that has a circular outer surface.

32. The tendon repair device of claim 26 that includes an antibiotic to inhibit the growth of bacteria.

33. The tendon repair device of claim 32 wherein the hollow tube is made of material and the antibiotic is included within the material.

34. The tendon repair device of claim 32 wherein the antibiotic is coated on the tube.

35. The tendon repair device of claim 26 that includes a growth enhancing agent.

36. The tendon repair device of claim 26 that has an inner surface and wherein the growth enhancing agent is on the inner surface.

37. The tendon repair device of claim 35 that is made of a material and the growth enhancing agent is included within the material.

38. The tendon repair device of claim 26 that has a textured inner surface to assist in retaining the first and the second end of the tendon.

39. The tendon repair device of claim 1 that includes a fabric.

40. The tendon repair device of claim 39 wherein the fabric is one or more of: woven, knitted, braided, and twisted.

41. The tendon repair device of claim 39 wherein the fabric comprises an absorbable material selected from the group consisting of: polyglactin, polycaprolate, poliglecaprone, polysorb, polyglygolic acid, polylactic acid, polydioxanone, caprolactone, collagen, surgical gut, and combinations thereof.

42. The tendon repair device of claim 39 wherein the fabric comprises a non-absorbable material selected from the group consisting of: polypropylene, polyester, nylon, silk, cotton, metal, and combinations thereof.

43. The tendon repair device of claim 25 that includes a fabric.

44. The tendon repair device of claim 43 wherein the fabric is one or more of: woven, knitted, braided, and twisted.

45. The tendon repair device of claim 43 wherein the fabric comprises an absorbable material selected from the group consisting of: polyglactin, polycaprolate, poliglecaprone, polysorb, polyglygolic acid, polylactic acid, polydioxanone, caprolactone, collagen, surgical gut, and combinations thereof.

46. The tendon repair device of claim 43 wherein the fabric comprises a non-absorbable material selected from the group consisting of: polypropylene, polyester, nylon, silk, cotton, metal, and combinations thereof.

* * * * *